United States Patent [19]

Armstrong

[11] Patent Number: 4,617,861
[45] Date of Patent: Oct. 21, 1986

[54] WHEY TREATMENT APPARATUS

[75] Inventor: Gordon M. Armstrong, Scotts Valley, Calif.

[73] Assignee: Fermentation Engineering, Inc., Manteca, Calif.

[21] Appl. No.: 433,239

[22] Filed: Oct. 7, 1982

[51] Int. Cl.$^4$ .............................................. A23C 21/00
[52] U.S. Cl. ...................................... 99/453; 99/456; 99/460; 366/165
[58] Field of Search .................... 426/582, 583, 36, 38, 426/41; 99/452–455, 456–459, 460, 465, 348, 483, 517, 275–277, 485; 366/136, 137, 165, 177, 167, 168

[56] References Cited

U.S. PATENT DOCUMENTS

| | | | |
|---|---|---|---|
| 2,630,060 | 3/1953 | Horneman et al. | 99/456 X |
| 2,967,773 | 1/1961 | Anderson | 426/510 X |
| 3,207,487 | 9/1965 | Ranson | 366/165 |
| 3,707,770 | 1/1973 | Timmins et al. | 426/492 X |
| 4,007,921 | 2/1977 | Zingg | 366/136 X |
| 4,123,800 | 10/1978 | Mazzei | 366/165 X |
| 4,333,958 | 6/1982 | Egnell | 426/582 X |

*Primary Examiner*—Timothy F. Simone
*Attorney, Agent, or Firm*—William B. Walker

[57] ABSTRACT

Cheese whey is treated to recover protein, convert the lactose to ethanol and recover the ethanol, and to provide a concentrated yeast with fermentation solubles concentrate. A sequence of treating whey by reverse osmosis, protein precipitation and separation, fermentation of concentrated lactose solution, distillation of the fermented product, dehydration of the hydrous ethanol product and evaporation of yeast fermentation solubles is described.

5 Claims, 7 Drawing Figures

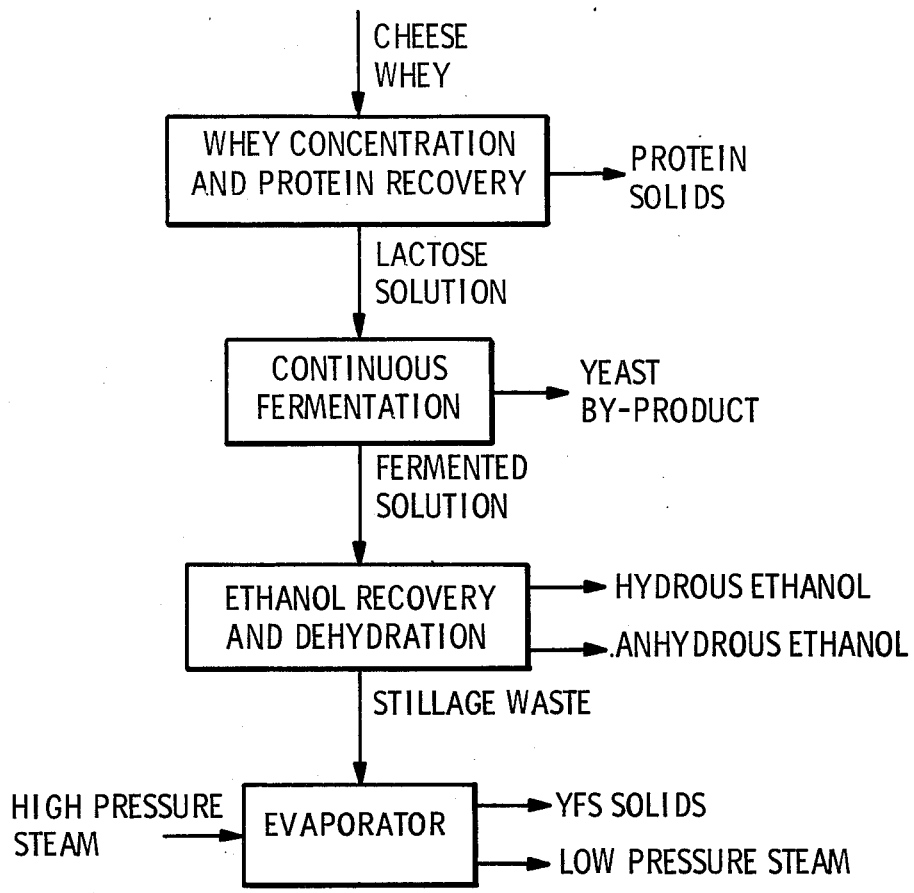
Fig_1
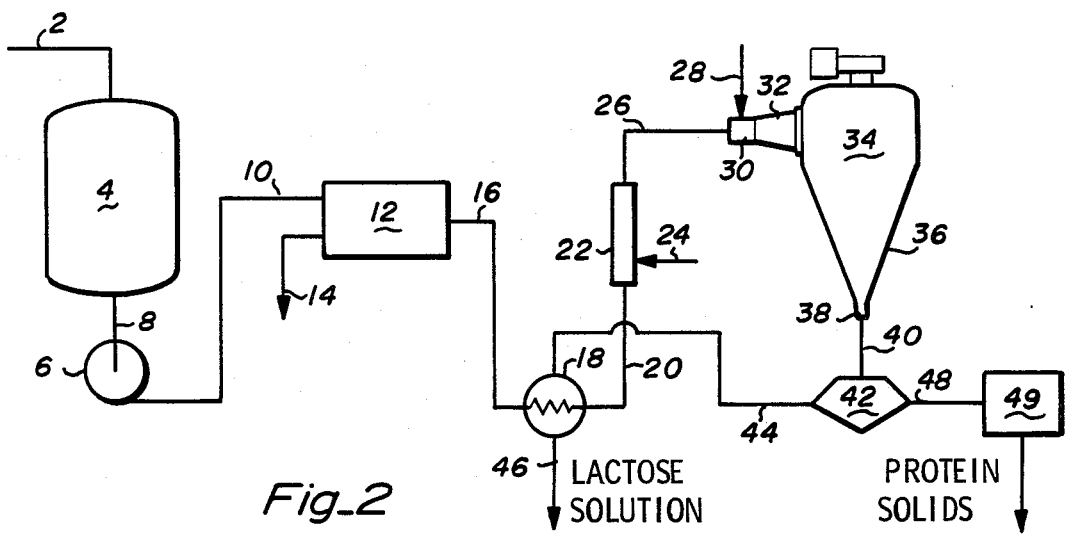
Fig_2

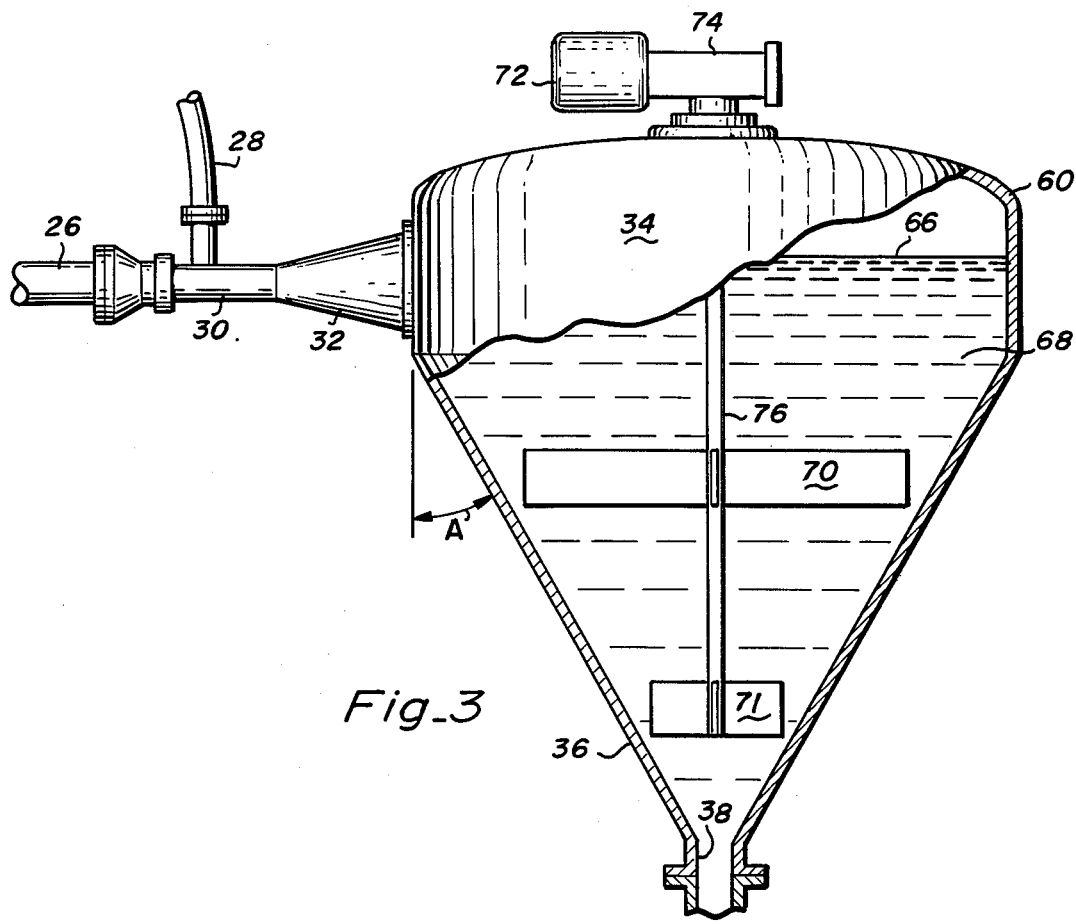
Fig_3
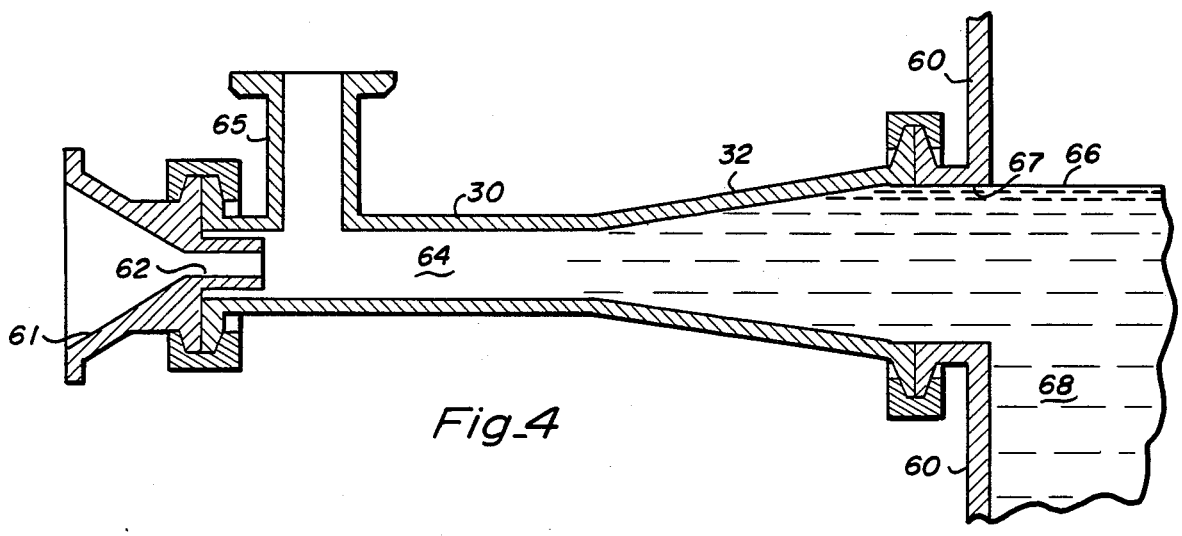
Fig_4

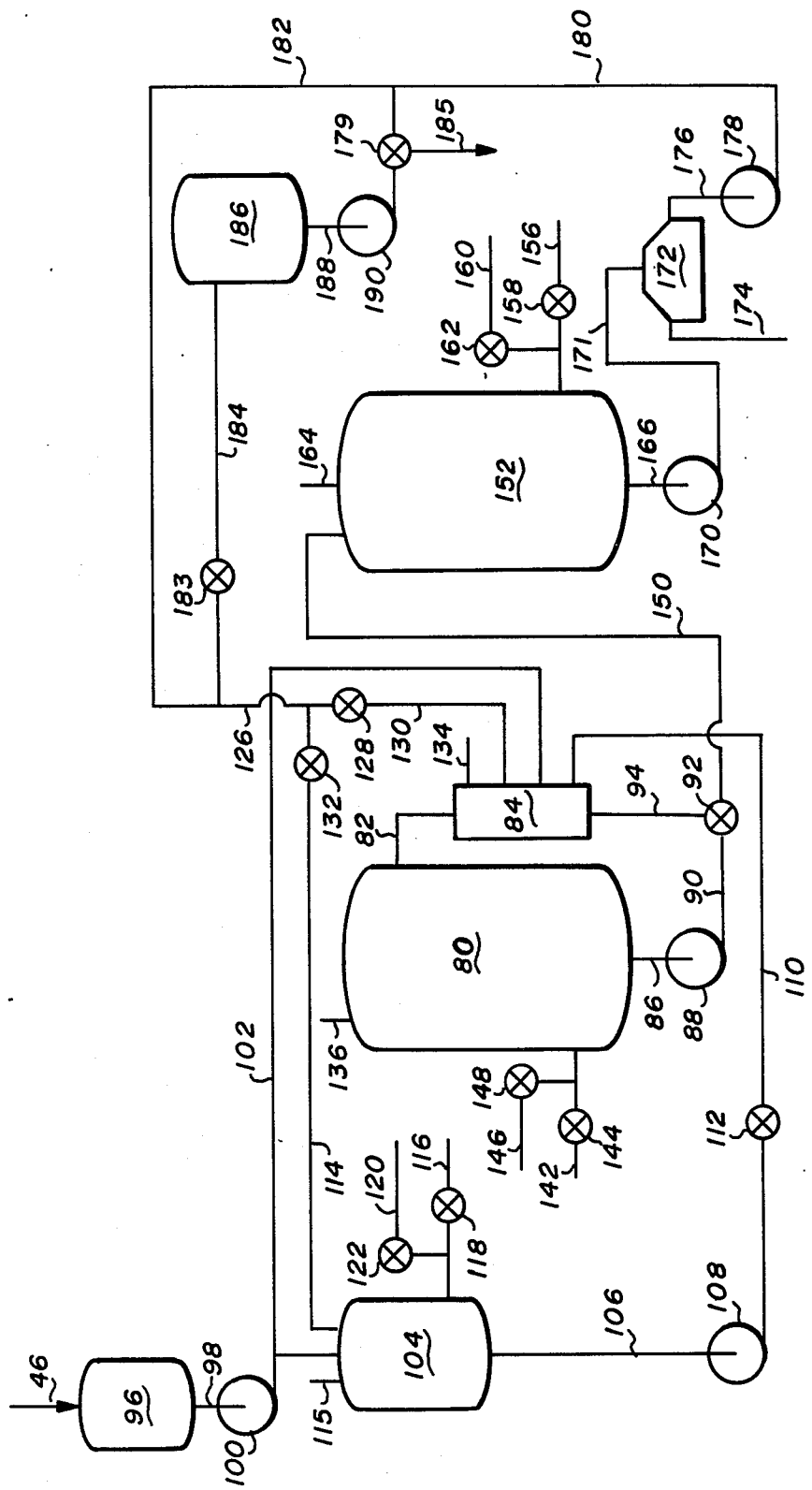
Fig._5

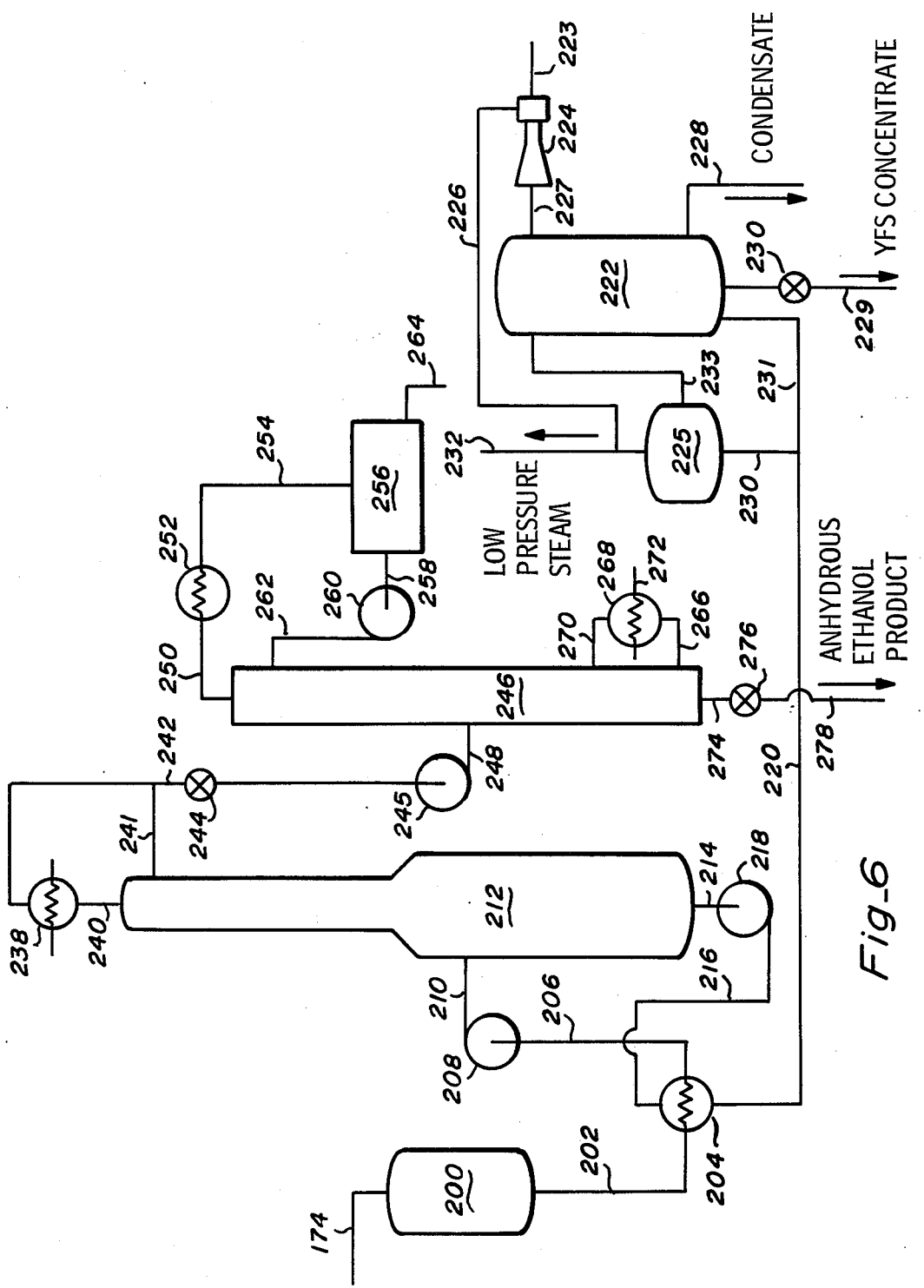
Fig_6

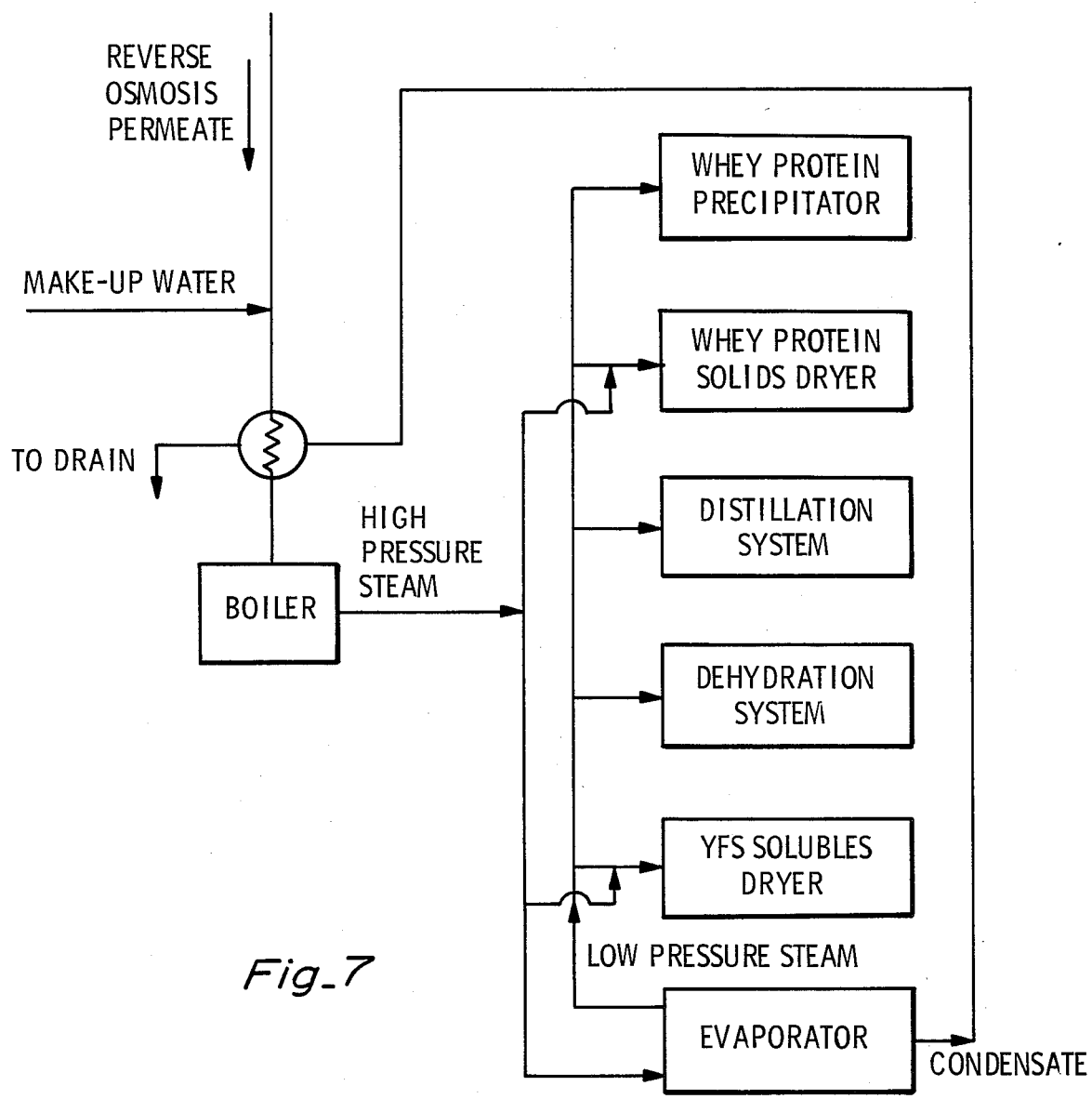
Fig_7

WHEY TREATMENT APPARATUS

FIELD OF THE INVENTION

This invention relates to the treatment of the whey by-product of cheesemaking to reduce the pollutants therein. More specifically, this invention relates to an apparatus and process for recovering useful products from whey process streams. More particularly, the apparatus and process of this invention recovers whey protein, converts whey lactose to ethanol, recovers the ethanol as a useful industrial fuel product, and yields a stillage concentrate of yeast with fermentation solubles useful as an animal feed supplement.

BACKGROUND OF THE INVENTION

Whey is the serum, or water, part of milk, which separates from the curds during the process of making cheese. Approximately 10 lbs of milk are used to produce 1 lb of cheese, and 9 lbs of whey are a by-product. It is the largest by-product of the huge U.S. dairy industry, and its disposal is a troublesome pollution problem.

DESCRIPTION OF THE PRIOR ART

U.S. Pat. No. 3,707,770 describes a method for recovering whey protein from cheese whey comprising ultrafiltration followed by reverse osmosis. In the ultrafiltration, a concentrated protein solution is formed, and the protein is recovered by spray drying the solution. The ultrafiltration permeate is treated by reversed osmosis to reduce the water content of the resultant lactose solution, and lactose is separated and recovered by subsequent procedures.

A related system has been described by C. E. Morris in *Food Engineering*, pp 67-72 (Jan. 1982). This system includes, in addition to the ultrafiltration and reverses osmosis steps, fermentation and distillation to convert the lactose product to ethanol. In this process, the ultrafiltration is used to provide a protein concentrate solution. The reverse osmosis removes water from the resulting lactose solution permeate which is then fermented. The ethanol product from the still is dehydrated to yield 199+ proof ethanol. A reversal of steps beginning with the reverse osmosis followed by ultrafiltration has also been suggested by T. P. Lyons et al in "Fuel Alcohol from Whey," *American Dairy Review* (Milk Products Edition) pp 42a–42e (Nov. 1980). Because ultrafiltration of highly concentrated solutions is not feasible with current technology, this alternate procedure has a disadvantage that only a limited amount of water can be removed in the reverse osmosis step so as to permit efficient ultrafiltration as a second step. Other articles describing systems for producing ethanol from whey are E. J. Mann, "Alcohol from Whey", *Dairy Industry International*, (March, 1980); and L. Reesan et al *Process Biochemistry*, pp 21, 22, 24 (November 1978).

OBJECTS AND SUMMARY OF THE INVENTION

This invention has the object to recover high quality alcohol and protein from whey, and to obtain a nutritious yeast with fermentation solubles (YFS) product useful in animal feeds as the final waste stream.

It is a further object of this invention to provide a process and apparatus for treating raw whey which, with optimized economic efficiency, essentially eliminates the disposal problem with these wastes and eliminates the need to have an elaborate sewage treatment system to reduce BOD.

It is still a further object of this invention to provide a continuous, easily automated whey process and recovery procedure having minimum energy requirements.

In summary, the apparatus of this invention is a cheese whey treating system comprising a whey concentrator, a whey protein precipitator, a whey protein separator, a yeast fermentation system, a distillation system, an ethanol dehydrator and an evaporator. The whey concentrator removes water from solutions containing whey protein and lactose. The whey protein precipitator mixes the whey protein concentrate with low pressure steam, and the whey protein solids formed are separated from the remaining lactose solution by the whey protein separator. The lactose solution is then fermented in the yeast fermentor, converting the lactose to ethanol. The ethanol is removed from the fermentation liquor by distillation and dehydrated. The stillage waste stream is concentrated in the evaporator to yield a yeast with fermentation soluble (YFS) by-product.

In summary, the protein precipitator of this invention comprises a precipitation vessel and a venturi mixer means for mixing incoming protein concentrate solution with low pressure steam, the outlet of the venturi mixer having diverging walls defining an expansion zone communicating with the precipitation vessel. Preferably, the precipitation vessel has cylindrical sidewalls and the bottom thereof is an inverted cone, the walls thereof forming an angle of less than 40° with the vertical axis of the vessel.

In summary, the process of this invention for treating cheese whey comprises initially removing water from the cheese whey while maintaining it at a temperature of less than 135° C. to increase the dissolved solids content to at least 10 weight percent, yielding a whey concentrate. The concentrate pH is adjusted to within the range of from 3.5 to 5.5 with an acidulant and is mixed with steam to raise the temperature of the whey concentrate to within the range of from 65° to 135° C. The protein precipitate is permitted to form as a particulate, easily separated protein precipitate, and the protein is separated from the solution, yielding a residual lactose solution. The protein precipitate is very fragile and easily broken. Additional steps in the process include converting the lactose to ethanol by yeast fermentation, recovering ethanol from the fermentation liquour by distillation and removing remaining water from the distillate to yield a 199+ proof ethanol product. The stillage waste is concentrated in an evaporator to yield a yeast with fermentation solubles (FYS) by-product.

BRIEF DESCRIPTION OF THE DRAWINGS

FIG. 1 is a schematic representation of the general process of this invention.

FIG. 2 is a schematic representation of the protein precipitation and lactose concentration system of this invention.

FIG. 3 is a partial cross-sectional view of the protein precipitator of this invention.

FIG. 4 is a cross-sectional view of the venturi mixer portion of the protein precipitator shown in FIG. 3.

FIG. 5 is a schematic representation of the yeast fermentation system of this invention.

FIG. 6 is a schematic representation of the distillation, dehydration and evaporator systems of this invention.

FIG. 7 is a schematic representation of the energy efficient steam generation and distribution system of this invention.

DETAILED DESCRIPTION OF THE INVENTION

Whey solutions derived from the manufacture of cheese solids typically have a high biological oxygen demand (BOD), and therefore, when discharged into waterways, create serious pollution problems.

Whey is the by-product of cheese manufacturing processes, one of which produces a sweet whey and the other an acid whey. Typical whey compositions are shown in Table A.

TABLE A

| Component | Concentration, wt. % | |
| --- | --- | --- |
| | Sweet Whey | Acid Whey |
| Water | 93 | 93 |
| Fat | 0.3 | 0.1 |
| Protein | 0.8 | 0.6 |
| Lactose | 4.9 | 4.3 |
| Ash | 0.56 | 0.46 |
| Lactic acid | 0.2–0.3 | 0.7–0.8 |

The variety of potentially valuable components found in the whey waste streams can be seen from the Table.

In the process of this invention, the valuable whey protein in the whey stream is recovered, the lactose remaining is converted to ethanol in a yeast fermentation system, and the fermentation by-product, now with enhanced nutritional value from the fermentation process, is concentrated to yield a yeast with fermentation solubles (YFS) which can be used as a livestock feed supplement. The protein recovered is edible and can also be used as a livestock feed supplement. The ethanol, particularly when dehydrated to a 199+ proof concentration, is useful as an octane enhancer when mixed with gasoline as in gasohol.

Referring to FIG. 1, a schematic representation of the process of this invention is presented. The cheese whey is first subjected to a whey concentration process followed by a protein recovery process, and whey protein solids are obtained as a by-product. The lactose solution from which the protein solids are separated is then treated in a continuous fermentation process according to this invention, yielding a yeast by-product. The fermentation liquor (beer) is treated to recover ethanol to yield hydrous ethanol which can be dehydrated to yield a 199+ proof (anhydrous) ethanol product. The stillage waste product is then evaporated and dried to yield YFS solids. The low pressure steam by-product of the evaporation step is used to provide heat in the distillation and protein recovery stages as will be explained in greater detail below with regard to FIG. 7.

Referring to FIG. 2, a schematic representation of the protein precipitation and lactose solution concentrating stage of the invention is shown. The whey stream 2 is fed into a storage tank 4 which functions as a surge tank. Pump 6 transports liquid from the holding tank outlet 8 through conduit 10 to the reverse osmosis system 12.

The reverse osmosis system is a conventional system such as that described in U.S. Pat. No. 3,707,770. It is operated at a pressure of greater than 400 psig, for example from 600–1000 psig and at a temperature of from 5° to 80° C. and preferably in the range of from 30° to 60° C. The reverse osmosis membranes can be comprised of a plurality of high pressure tubes, that is, tubes such as cellulose acetate membranes cast directly inside an epoxy resin reinforced, braided glass fiber tube. Depending upon the choice of membrane, all compounds having molecular weights greater than as low as 30 including the proteins, lactose, and non-protein nitrogen acids can be retained. The solution is concentrated to at least 10 weight percent solids, preferably above 15 weight percent solids and optimally at least 17.5 weight percent solids. Conduit 14 carries low BOD permeate liquid containing minor low molecular weight compounds and water removed from the whey stream for disposal.

The reverse osmosis retentate outlet conduit 16 leads to heat exchanger 18 where the protein concentrate is heated by the lactose solution passed through the heat exchanger by conduit 44. The heated protein concentrate solution is directed from the heat exchanger 18 through conduit 20 to the chemical pH adjustment contact chamber 22. Here, the protein concentrate is acidified to a protein precipitation pH with an acidulator such as phosphoric acid introduced through inlet conduit 24. PH adjustment to within the range of from 4.5 to 4.7 is preferred.

The protein concentrate solution is then fed by conduit 26 to the venturi mixer 30 where the input stream is mixed with low pressure steam delivered by steam conduit 28. The mixture of steam and protein concentrate solution is then passed through the inlet 32 having diverging walls to the protein precipitator 34. The protein precipitator 34 has a bottom section which is an inverted cone as described in greater detail with respect to FIG. 3. The protein precipitate-lactose solution mixture formed in the precipitator is transported from the precipitator outlet 38 through conduit 40 to the separator 42. Preferably the precipitator outlet 38 is positioned at a higher elevation than the separator 42 so that gravity flow discharge or a similar technique can be used to convey the fragile protein floc to the separator. Agitation and break-up of the floc prior to separation reduces protein recovery, makes separation more difficult and is therefore preferably avoided. The liquid phase removed from the protein solids in the separator 42 is fed by conduit 44 to heat exchanger 18 where it heats incoming protein concentrate. The cooled solution is transported from the heat exchanger 18 through conduit 46 to the fermentation system shown in FIG. 5. The protein solids removed by the separator 42 are transported to protein dryer 49 through conduit 48.

The whey protein solids which are separated as a wet cake may be used in that form, dewatered further using a roller or belt press to produce a dryer, higher protein content cake, or may be sent to a dryer. Since the protein is already denatured, a high heat dryer such as a drum dryer can be used for drying the product. A spray dryer is also suitable.

Referring to FIG. 3, a partial cross-sectional representation of the protein precipitator is shown. In general, the protein precipitator 34 preferably has a cylindrical sidewall 60 and a bottom 36 which has the shape of an inverted cone. The conical section 36 forms an angle A of less than 40° with the vertical cylindrical sidewall (and with the central axis of the precipitator which is parallel thereto).

Referring to FIG. 4, a cross-sectional view of the venturi steam mixer is shown, and FIGS. 3 and 4 can be considered together in this respect. The protein concentrate solution is fed by conduit 26 to the inlet 61 of the venturi mixer 30. Passing through the restriction 62 into the mixing chamber 64, the protein solution is mixed with low pressure steam provided through conduit 28 to the steam inlet 65. An intimate solution-steam mixture occurs within the mixing chamber 64, and the resulting mixture passes between the diverging wall 32 to the precipitator inlet 67. The liquid level 66 in the precipitator is maintained at the same level as the top of the inlet 67 to minimize agitation in the precipitator 60 from the incoming stream. The steam heated mixture effectively denatures the soluble protein constituents, and the less soluble denatured protein precipitates and forms a loose flock dispersed in the solution 68. Gentle agitation is provided by the agitator blades 70 and 71 to insure adequate residence time (prevent short circuiting). The agitator motor 72 operating through reduction gear box 74 turns the shaft 76 at a low rpm so that a gentle agitation is provided. Excessive agitation disrupts the protein flock and causes re-homogenization of the protein. The steeply angled bottom wall 36 does not provide a surface on which the protein flock can collect due to its steep slope. The protein precipitate flows to the bottom of the precipitator 60 and is removed through precipitator outlet 38. By minimizing tunneling, the material removed through outlet 38 has a maximized residency time. This method of whey protein recovery is designed to maximize the amount of protein recovered when utilizing a heat-acid precipitation process. The protein is handled in such a way as to reduce the amount which is resolubilized.

Referring to FIG. 5, the yeast fermentation system of this invention is illustrated. Specific details of this system are described in copending application Ser. No. 159,953 filed June 16, 1980. Lactose solution from the centrifugal separator 42 is fed through line 46 to the surge tank 96. Proteolytic enzymes can be added to the contents of surge tank 96 to reduce any proteins remaining in the lactose solution to amino acids. This not only provides a nitrogen nutrient source for the fermentation but avoids problems which would occur in the yeast recycle system if suspended whey protein solids were to accumulate. Fresh lactose solution from holding tank 96 is fed through outlet 98 through pump 100 and conduit 102 to the contact chamber 84. Contact chamber 84 insures that the yeast, nutrients and concentrated lactose solution have a controlled contact time of not less than 10 seconds before being introduced into anaerobic fermentation vessel 80 through inlet conduit 82. The solution is continuously removed through outlet 86 by pump 88 and recycled through conduit 90, valve 92 and conduit 94 to the contact chamber 84 to control the contact time and lactose concentration in the fermentor 80. Aerobic fermentor 104 provides fresh yeast to the fermentation system. A yeast suspension is fed through outlet 106 and pump 108 to conduit 110 as controlled by control valve 112. The fresh yeast is introduced when and at the rate desired into contact chamber 84 containing incoming concentrated lactose solution, recycled yeast and nutrients, and is thereby introduced to fermentation vessel 80. The aerobic fermentation vessel 104 is provided with seed yeast from the fermentation yeast recycle system through conduit 115. The aerobic fermentor also has a nutrient inlet 110. Air supply conduit 116 communicates with the aerobic fermentor through valve 118. Ammonia introduced into fermentor 104 from ammonia supply conduit 120 through valve 122 provides pH control and nutrients for yeast growth.

Yeast from the yeast circulation system (pump 190, conduit 182, valve 183, and conduit 184) is fed to the fermentation vessel 80 through conduit 126, valve 128 and conduit 130 leading to the contact chamber 84. Seed yeast supply to the aerobic fermentor 104 is provided through control valve 132 and line 114. Yeast return to tank 186 is controlled by valve 183. Tank 186 is a storage and/or treatment tank.

Fermentation vessel 80 is supplied with nutrients and other chemicals through conduits 134 and 136. Air supply conduit 142 communicates with the vessel 80 through valve 144. Ammonia inlet for pH control is provided by ammonia supply conduit 146 communicating with fermentor 80 through valve 148.

As directed by valve 92, after initial fermentation, fermentation product from fermentation vessel 80 is pumped by pump 88 through conduit 90, valve 92 and conduit 150 to the second anaerobic fermentation vessel 152 where fermentation is completed. The fermentation broth transferred to fermentor 152 has less than half the lactose concentration of the original concentrated lactose solution fed to fermentor 80, and the rate of transfer is controlled to maintain a steady lactose concentration in fermentor 80 of less than 6 and preferably less than 3 weight percent. Thus, at least 50 percent of the lactose is used in the fermentor 80 and the remainder is used in fermentor 152. Air supply conduit 156 communicates through valve 158 with vessel 152 to provide air needed for microaeration to maintain a desired fermentation rate. Ammonia supply conduit 160 operating through valve 162 provides ammonia to fermentation vessel 152 for pH control and nutrient nitrogen. Nutrients and other chemical adjuncts can be supplied to fermentation vessel 152 through conduit 164.

After fermentation is completed in vessel 152 the fermented product (beer) is removed through outlet 166 and fed by pump 170 and conduit 171 to the yeast separator 172. The fermented solution containing ethanol is removed for further processing through conduit 174. The yeast concentrate removed by the separator 172 is removed through conduit 176 and pumped by pump 178 to conduit 180 and to the yeast recirculation system (Conduits 182, 126, 114 and 184). Conduit 182 supplies yeast as a constantly circulating suspension to the anaerobic fermentor 80 and aerobic fermentor 104, and return line 184 returns the unused yeast suspension to the yeast storage and/or treatment reservoir 186. By-product yeast is removed through valve 179 to conduit 185. Circulation is provided through the reservoir outlet 188 and pump 190 through the line 182 and return line 184.

Referring to FIG. 6, fermentation product (beer) from the yeast separator 172 (shown in FIG. 5) is fed through conduit 174 to a holding tank 200. From this holding vessel, the fermentation product is fed through conduit 202 through heat exchanger 204 where it is heated by the stillage stream. It is fed through conduit 206, pump 208 and column inlet 210 to the distillation column 212. The distillation column 212 is a conventional distillation column. The stillage outflow through still outlet 214 is pumped through conduit 216 and through heat exchange 204 by pump 218. Conduit 220 transfers the column stillage from the heat exchanger 204 to the evaporator 222.

The evaporator 222 has a high pressure steam inlet conduit 223 leading to a thermocompressor 224 which entrains vapor from the vapor separator 225 provided through conduit 226. This effects an increase in production of low pressure steam to conduit 227. The low pressure steam is directed to the shell side of the evaporator through conduit 227. Hot condensate from the evaporator is fed by conduit 228 to a boiler make-up water preheater (not shown). The YFS concentrate is removed through YFS outlet valve 230 to YFS outlet conduit 229. The distillation column stillage (through conduit 220) and liquid from the separator 225 (through conduit 230) are introduced to the tube side of the evaporator 222 through conduit 231. Saturated steam (and entrained liquid) is carried from the evaporator 222 to the separator 225 by conduit 233. Excess steam is carried by conduit 232 to other parts of the system as described with respect to FIG. 7.

The distillation column 212 has a vapor condensor 238 at the top thereof, the vapor rising through conduit 240, and the condensate returning through conduit 241 to the top of the still to maintain the desired reflux ratio. The distillate is removed from the top of the column as controlled by valve 244 and fed by pump 245 to the dehydration column 246 through conduit 248. In the dehydration column 246, an azeotrope breaking solvent is used to remove the bound water remaining in the hydrous ethanol. Any solvent normally used to break ethanol-water azeotropic mixtures can be used. Isopropyl ether is a preferred solvent in this system. The isopropyl ether-water vapor (containing a minor amount of ethanol) leaves the dehydration column 246 through the vapor outlet 250 and passes through the condenser 252 where the vapors are condensed. The liquid mixture passes through conduit 254 to the liquid separator 256 where, the cooled condensate separates. The water-ethanol fraction is recycled to the distillation column 212. The isopropyl ether is removed through conduit 258 and is pumped by pump 260 to the azeotrope breaking solvent inlet to the dehydration column 262. The anhydrous ethanol collecting at the bottom of the dehydration column 246 communicates with heat exchanger 268 through recycle conduit 266. Here in the heat exchanger 268, low pressure steam is used to vaporize a portion of the ethanol, the vapor exiting at 270 and entering the column to provide heat thereto. Anhydrous ethanol (199+ proof) is removed through the ethanol product outlet and through ethanol product valve 276 to the anhydrous ethanol product outlet conduit 278.

Referring to FIG. 7, a schematic representation of the steam generation and distribution system is shown. High pressure steam from the boiler is fed to the evaporator system, the condensate being recycled to the boiler make-up water preheater. Low pressure steam from the shell side of the evaporator is fed to the whey protein precipitator, whey solids dryer, distillation system, dehydration system and YFS solubles dryer to provide heat requirements. Supplemental heat in the form of high pressure steam is provided to the whey protein dryer and YFS solubles dryer, as needed.

The whey treatment system of this invention can be seen to be a major improvement over those previously known in the efficiency of operation, the quality of protein, ethanol and FYS products obtained, the low pollutant loading in discharge streams, the low energy consumption required in this system, and the total recovery of all valuable whey components. The energy remaining in the low pressure steam produced in the evaporator, because of the unique design of this system, can be advantageously used in other portions of the system requiring heating. Because the biodegradable components in the whey strain are completely converted to useful products, this system entirely eliminates waste disposal problems present with previously systems.

This invention is further illustrated by the following specific but non-limiting example showing the operation of the system.

EXAMPLE 1

This example illustrates the continuous treatment of 435,000 gallons per day of sweet whey having the following composition:

TABLE B

| Component | Conc., wt. % |
|---|---|
| Water | 93.8 |
| Fat | 0.05 |
| Protein | 0.7 |
| Lactose | 4.5 |
| Ash | 0.6 |
| Lactic acid | 0.15 |
| Non-protein nitrogen | 0.2 |

The whey solution is treated by reverse osmosis, employing Paterson Candy International, Ltd. membranes ZF-99 at a pressure of over 500 psig. Sufficient water is removed to yield a final concentration of 1.98 weight percent protein. The protein concentrate is then passed through a heat exchanger where its temperatures is raised to 71° to 75° C. by heat obtained from the lactose solution. Its pH is adjusted to 4.65 by adding phosphoric acid. It is mixed with sufficient low pressure steam to elevate the temperature to from 90° to 95° C. and introduced into a precipitator. The heat required is 276 lb per hour of low pressure steam at 219° C. The average residence time in the precipitator is 10 to 15 min., and the quantity of true protein produced (dry basis) is 80 lb per hour. After separation of the protein precipitate, the remaining lactose solution has concentration of 12.6 weight percent lactose. The lactose solution is then transported to a holding tank where it is retained until being introduced to the fermentation system.

The lactose solution is fed to the first fermenter. The pH is adjusted to 4.5 and nutrients are added. Sources of ammonium ions such as anhydrous ammonia, ammonium phosphate or ammonium sulfate; phosphate ions such as sodium phosphate, dipotassium phosphate or ammonium phosphate; and sources of vitamins and other growth factors such as yeast extract are added. Fresh yeast and older yeast recovered from the fermentation products are mixed to provide a yeast concentration of 3.2 wt. % (dry basis). The average residence time in the first fermentor is 12 hours, that is, long enough to provide an average of less than 6 wt. % lactose in the solution. Liquid is then fed to the second fermenter where fermentation is completed. The operation is carried out at a temperature of 35° C., with an adjusted pH of 4.5 and with added nutrient sources of phosphate and ammonium ions and factors such as yeast extract. Fermentation is complete after an additional average residence time of 12 hours. The ethanol percentage in the solution is approximately 6.0 wt. %, and only 0.5 wt. % lactose remains.

Fresh yeast added to the lactose solution for the first fermentation was obtained from an aerobic fermentor operating at a temperature of 35° C. and a pH of 3.5, using as nutrient sources of phosphate and ammonium ions and vitamins and factors as described above. 105 CFM of air is continuously added to the system to maintain a desired oxygen saturation.

The fermented liquid (beer) is then transported to a holding tank from which the distillate column feed is obtained. The feed to the distillation column is 5372 gallons per hour of ethanol solution. The distillation column ethanol output is 335 lbs per hour of ethanol having a concentration of 195 proof. Approximately 5052 lbs per hour stillage is removed, and passed through a heat exchanger where it heats the incoming fermentation product (beer) prior to its introduction to the distillation column. The cooled stillage having a temperature of 70° C. is fed to the evaporator. With an inflow of 594 gallons per hour of stillage, sufficient high pressure steam is provided to the evaporator to yield a YFS product having a 40 wt. % solids content and generating 2300 lbs per hour of low pressure steam having a temperature of 104° C. The amount of high pressure steam required is 2800 lbs per hour at 182° C. and 150 psig. The FYS output is approximately 70 gallons per hour. In the dehydration column, 335 gallons per hour of 195 proof ethanol is fed to the column where it is contacted with isopropyl ether. A vapor mixture containing ethanol, water and isopropyl ether is obtained, condensed and fed to a decanter where the isopropyl ether is recovered. Water removed in the dehydration process containing about 50 wt. % ethanol is recycled to the distillation column to recover the ethanol. The 199+ ethanol output of the column is 320 gallons per hour.

The invention claimed is:

1. A cheese whey treating system comprising
   (a) a whey protein concentrator having an outlet for removing water from whey,
   (b) a whey protein precipitator communicating with the outlet of the whey protein concentrator and comprising a steam injector means for mixing the concentrated whey solution with steam, the whey protein precipitator having an outlet,
   (c) a whey protein separator communicating with the outlet of the whey protein precipitator for separating precipitated protein solids from liquid, the liquid being a lactose solution, the whey protein separator having a lactose solution outlet,
   (d) a fermentation means communicating with the lactose solution outlet, for converting lactose in the lactose solution to ethanol, the fermentation means having a fermented
   (e) distillation means communicating with the fermented product outlet for separating ethanol from the fermented product, the distillation means having a distillate outlet and a stillage outlet,
   (f) dehydrator means communicating with the distillate outlet for removing water remaining in the distillate, and
   (g) evaporator means communicating with the stillage outlet for concentrating the stillage to yield a yeast with fermentation solubles concentrate.

2. The cheese whey treating system of Claim 1 wherein the whey protein precipitator comprises a precipitation vessel and a venturi mixer means for mixing incoming whey protein concentrate with low pressure steam, the venturi mixer outlet having diverging walls defining an expansion zone communicating with the precipitation vessel.

3. The cheese whey treating system of claim 2 wherein the precipitation vessel is cylindrical, and the bottom thereof is an inverted cone, the walls of the cone forming an angle of less than 40° with the vertical axis of the vessel.

4. The cheese whey treating system of claim 2 wherein the whey protein separator is a centrifugal decanter means.

5. The cheese whey treating system of claim 1 wherein the whey protein concentrator is a reverse osmosis means.

* * * * *